United States Patent
Steiger et al.

(10) Patent No.: US 9,812,330 B2
(45) Date of Patent: Nov. 7, 2017

(54) FORMULATIONS FOR PRODUCING INDIUM OXIDE-CONTAINING LAYERS, PROCESS FOR PRODUCING THEM AND THEIR USE

(71) Applicant: Evonik Degussa GmbH, Essen (DE)

(72) Inventors: Juergen Steiger, Taipei (TW); Alexey Merkulov, Recklinghausen (DE); Arne Hoppe, Herne (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/900,821

(22) PCT Filed: Apr. 28, 2014

(86) PCT No.: PCT/EP2014/058615
§ 371 (c)(1),
(2) Date: Dec. 22, 2015

(87) PCT Pub. No.: WO2014/206599
PCT Pub. Date: Dec. 31, 2014

(65) Prior Publication Data
US 2016/0141177 A1    May 19, 2016

(30) Foreign Application Priority Data
Jun. 25, 2013 (DE) .................. 10 2013 212 019.2

(51) Int. Cl.
| C07F 5/00 | (2006.01) |
| H01L 21/288 | (2006.01) |
| C23C 18/12 | (2006.01) |
| C23C 18/14 | (2006.01) |
| C23C 16/46 | (2006.01) |
| C23C 16/48 | (2006.01) |
| H01L 21/02 | (2006.01) |
| C23C 16/40 | (2006.01) |

(52) U.S. Cl.
CPC ............. *H01L 21/288* (2013.01); *C07F 5/00* (2013.01); *C23C 16/407* (2013.01); *C23C 16/46* (2013.01); *C23C 16/48* (2013.01); *C23C 18/1216* (2013.01); *C23C 18/14* (2013.01); *H01L 21/02381* (2013.01); *H01L 21/02488* (2013.01); *H01L 21/02565* (2013.01); *H01L 21/02623* (2013.01); *H01L 21/02628* (2013.01); *H01L 21/02664* (2013.01)

(58) Field of Classification Search
CPC ........ C07F 5/00; C07F 5/003; C23C 18/1291; H01L 21/288
USPC .................................................. 556/1
See application file for complete search history.

(56) References Cited

U.S. PATENT DOCUMENTS

| 8,546,594 B2 | 10/2013 | Steiger et al. |
| 8,580,989 B2 | 11/2013 | Steiger et al. |
| 8,841,164 B2 | 9/2014 | Steiger et al. |
| 8,859,332 B2 | 10/2014 | Steiger et al. |
| 9,115,422 B2 | 8/2015 | Steiger et al. |
| 9,194,046 B2 | 11/2015 | Hoppe et al. |
| 9,293,326 B2 | 3/2016 | Steiger et al. |
| 9,315,901 B2 | 4/2016 | Steiger et al. |
| 2012/0289728 A1* | 11/2012 | Steiger .................. C07F 5/003 556/1 |
| 2013/0104773 A1 | 5/2013 | Steiger et al. |
| 2013/0116463 A1* | 5/2013 | Steiger .................. C07F 5/069 556/1 |
| 2016/0159824 A1 | 6/2016 | Steiger et al. |

FOREIGN PATENT DOCUMENTS

| DE | 10 2010 031592 A1 | 1/2012 |
| WO | 2011/072887 A1 | 6/2011 |

OTHER PUBLICATIONS

International Search Report dated Jul. 16, 2014 in PCT/EP14/58615 Filed Apr. 28, 2014.

* cited by examiner

*Primary Examiner* — Sudhakar Katakam
*Assistant Examiner* — Kofi Adzamli
(74) *Attorney, Agent, or Firm* — Oblon, McClelland, Maier & Neustadt, L.L.P.

(57) ABSTRACT

The present invention relates to liquid formulations which can be produced by dissolving at least one indium alkoxide compound which can be prepared by reacting an indium trihalide $InX_3$ where X=F, Cl, Br, I with a secondary amine of the formula $R'_2NH$ where R'=alkyl in a molar ratio of from 8:1 to 20:1 to the indium trihalide in the presence of an alcohol of the generic formula ROH where R=alkyl in at least one solvent, a process for producing them, their use for producing indium oxide-containing or (semi)conducting layers and processes for producing indium oxide-containing layers which use the formulation of the invention.

15 Claims, 1 Drawing Sheet

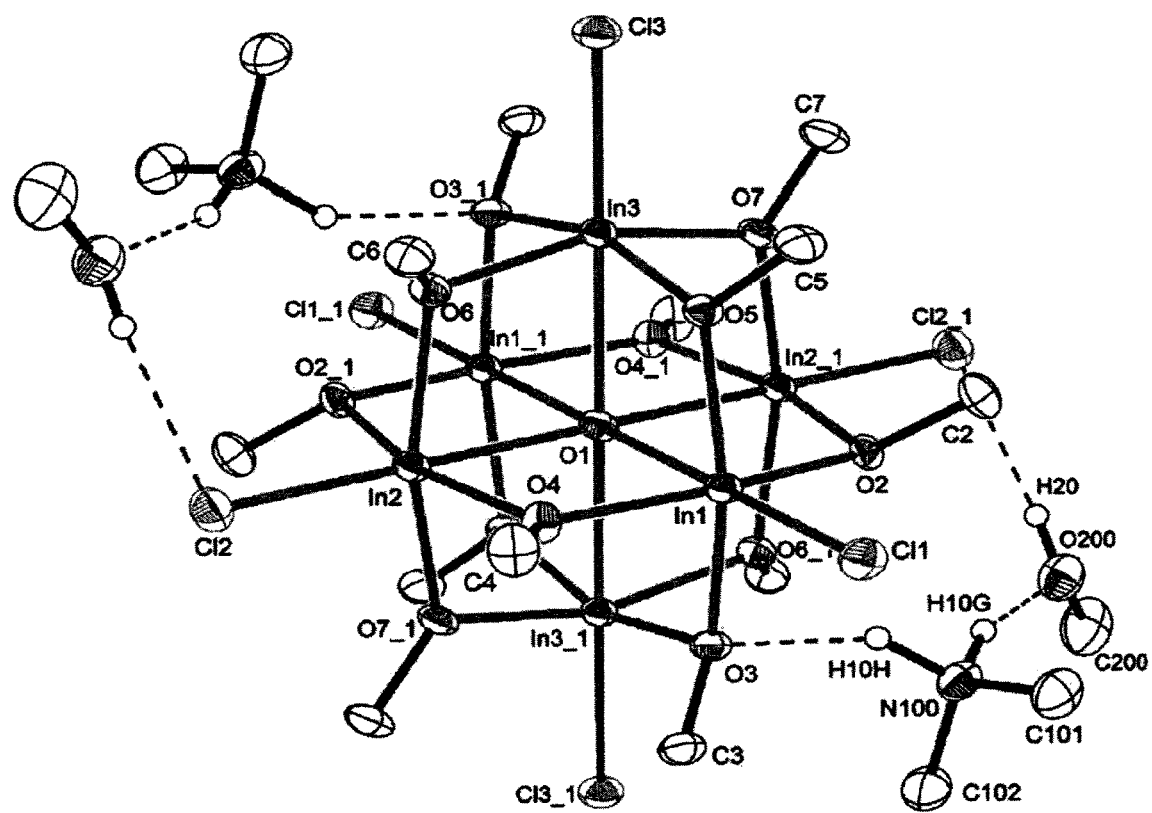

FORMULATIONS FOR PRODUCING INDIUM OXIDE-CONTAINING LAYERS, PROCESS FOR PRODUCING THEM AND THEIR USE

The present invention relates to formulations for producing indium oxide-containing layers, a process for producing them and their use.

The production of semiconducting electronic component layers by means of pressure deposition processes and other liquid deposition processes makes it possible to achieve far lower production costs compared to many other processes, e.g. chemical vapour deposition (CVD), since the deposition of the semiconductor can in this case be carried out in a continuous process. In addition, in the case of relatively low process temperatures, there is the opportunity of also working on flexible substrates and optionally achieving optical transparency of the printed layers (especially in the case of very thin layers and in particular in the case of oxidic semiconductors). Here and in the following, the term semiconducting layers is used to refer to layers which have a charge carrier mobility of from 1 to 50 $cm^2/Vs$ in a component having a channel length of 20 μm at a gate-source voltage of 50 V and a source-drain voltage of 50 V.

Since the material of the component layer to be produced by printing processes to a critical extent determines the respective layer properties, the choice of this material has a significant influence on every component containing this component layer. Important parameters for printed semiconductor layers are their respective charge carrier mobilities and the processabilities and processing temperatures of the printable precursors used in the production of the layers. The materials should have a good charge carrier mobility and be able to be produced from solution and at temperatures significantly below 500° C. in order to be suitable for a large number of applications and substrates. It would likewise be desirable for the semiconducting layers produced to be optically transparent for many new types of applications.

Indium oxide (indium(III) oxide, $In_2O_3$) is, owing to the large band gap in the range from 3.6 to 3.75 eV (measured on vapour-deposited layers, H. S. Kim, P. D. Byrne, A. Facchetti, T. J. Marks; J. Am. Chem. Soc. 2008, 130, 12580-12581), a very promising and thus desirable conductor. Thin films of a few hundred nanometres in thickness can additionally have a high transparency in the visible spectrum of greater than 90% at 550 nm. In addition, charge carrier mobilities of up to 160 $cm^2/Vs$ can be measured in extremely highly ordered indium oxide single crystals. However, such values have hitherto not been able to be achieved by processing from solution (H. Nakazawa, Y. Ito, E. Matsumoto, K. Adachi, N. Aoki, Y. Ochiai; J. Appl. Phys. 2006, 100, 093706, and A. Gupta, H. Cao, Parekh, K. K. V. Rao, A. R. Raju, U. V. Waghmare; J. Appl. Phys. 2007, 101, 09N513).

Indium oxide is often used, especially together with tin(IV) oxide ($SnO_2$), as semiconducting mixed oxide ITO. Owing to the relatively high conductivity of ITO layers combined with transparency in the visible spectrum, it is used, inter alia, in the field of liquid crystal displays (LCD), especially as "transparent electrode". These usually doped metal oxide layers are produced industrially mainly by costly vapour deposition methods in a high vacuum. Owing to the great economic interest in ITO-coated substrates, there are now some coating processes, especially processes based on sol-gel techniques, for indium oxide-containing layers.

There are in principle two possibilities for producing indium oxide semiconductors by printing processes: 1) particle concepts in which (nano)particles are present in a printable dispersion and are converted after the printing operation into the desired semiconductor layer by means of sintering processes, and 2) precursor concepts in which at least one soluble or dispersible intermediate is converted after printing of an appropriate composition into an indium oxide-containing layer. The particle concept has two important disadvantages compared to the use of precursors: firstly, the particle dispersions have a colloidal instability which makes it necessary to employ dispersing additives (which are disadvantageous in respect of the later properties of the layer), and secondly many of the particles which can be used form only incomplete layers by means of sintering (e.g. due to passivation layers), so that particulate structures still occur to some extent in the layers. There is a considerable particle-particle resistance at the particle boundaries and this reduces the mobility of the charge carriers and increases the general layer resistance.

There are various precursor-containing formulations for producing indium oxide layers. Thus, it is possible to use not only indium salts but also indium alkoxides (homoleptic compounds, i.e. compounds comprising only indium and alkoxide radicals) as precursors in solution for producing indium oxide-containing layers.

For example, Marks et al. describe components in the production of which a precursor-containing composition comprising the salt $InCl_3$ and the base monoethanolamine (MEA) are used as a solution in methoxyethanol. After application of the composition by spin coating, the corresponding indium oxide layer is produced by thermal treatment at 400° C. (H. S. Kim, P. D. Byrne, A. Facchetti, T. J. Marks; J. Am. Chem. Soc. 2008, 130, 12580-12581 and supplemental information).

WO 2011/072887 A1 describes a process for preparing indium(III) halide dialkoxides and their use for producing indium oxide-containing layers. Processes for producing indium oxide-containing layers from these indium(III) halide dialkoxides are disclosed in WO 2011/073005 A2.

Indium(III) halide dialkoxides in solution have however hitherto not led to indium oxide-containing layers having sufficiently good electrical properties. Indium oxoalkoxides, for example the compounds of the generic formulae $In_6O_2X_6(OR)_6(R'CH(O)COOR'')_2(HOR)_x(HNR''')_2)_y$, $In_7O_2(OH)(OR)_{12}X_4(ROH)_x$ and $M_xO_y(OR)_z[O(R'O)_eH]_aX_bY_c[R''OH]_d$ disclosed in WO 2012/010427 A1, WO 2012/010464 A1 and in the as yet unpublished German application DE 10 2012 209918, lead to better layer properties.

Despite the improvements already known, there is a continuing need for improvements in respect of the layer forming properties and the properties of the layers obtained. In particular, a suitable precursor-containing solution should be able to be processed readily, in particular in air,
be able to be converted homogeneously into the oxide,
be able to be converted into the oxide at very low temperatures and
lead to layers having excellent electrical properties.

This complex requirement profile is met by the liquid formulation according to the invention which can be produced by dissolving at least one indium alkoxide compound which can be prepared by reacting an indium trihalide $InX_3$ where X=F, Cl, Br, I
with a secondary amine of the formula $R'_2NH$ where R'=alkyl,
in a molar ratio of from 8:1 to 20:1 to the indium trihalide in the presence of an alcohol of the generic formula ROH where R=alkyl in at least one solvent.

Particularly good layers can be produced using formulations containing indium alkoxide compounds in whose preparation the secondary amine has been used in a molar ratio of from 8:1 to 15:1, even better in a ratio of from 8:1 to 12:1, to the indium trihalide in the reaction.

BRIEF DESCRIPTION OF THE DRAWING

FIG. 1 shows the structure of $[In_6(O)(OMe)_{12}Cl_6]^{2-}[NH_2R_2]^+_2(MeOH)_2$, which can be prepared using $InCl_3$, $Me_2NH$ (the latter in a ratio of from 9:1 to 10:1) and MeOH (methanol), as determined by X-ray structure analysis.

For the purposes of the present invention, an indium alkoxide compound is in the present case a compound which has at least one indium atom and at least one alkoxide radical and can be prepared by the above-described reaction of the trihalide with the secondary amine in the presence of an alcohol. Determination of the structure of these dissolved compounds which can be obtained by the process of the invention is difficult. However, it is assumed that the resulting compounds are halogen-containing indium oxoalkoxide compounds. Solid-state structures of this type have been able to be determined by means of X-ray structure analysis. It is assumed that similar structures for these compounds are also present in solution. Indium oxoalkoxides are indium clusters which are bridged by oxo radicals and may be present in ionic form and in which valencies which are not coordinated by oxo radicals are at least partly coordinated by alkoxide radicals. In the case of the indium alkoxide compounds which can be obtained by the process of the invention, it is assumed that they are usually present as salt, in particular as halogen-containing indium oxoalkoxide anions coordinated by cations, after the synthesis.

A particularly preferred process product is an indium alkoxide compound of the generic formula $[In_6(O)(OR)_{12}X_6]^{2-}A_m^z(ROH)_x$ where R=alkyl, X=F, Cl, Br, I, A=cation, z=valency of the cation, m·z=2 and x=0 to 10, which can be prepared, inter alia, using secondary amines in a ratio of from 9:1 to 10:1. The compound can be coordinated by alcohol molecules ROH and possibly also by other solvents present in the reaction.

Typical cations are ammonium ions $[NH_yR_{4-y}]^+$, preferably ammonium ions of the formula $[NH_2R_2]^+$.

A very particularly preferred compound is $[In_6(O)(OMe)_{12}Cl_6]^{2-}[NH_2R_2]^+_2(MeOH)_2$, which can be prepared using $InCl_3$, $Me_2NH$ (the latter in a ratio of from 9:1 to 10:1) and MeOH (methanol). The structure of this as determined by X-ray structure analysis is shown in FIG. 1.

The formulation of the invention preferably contains the indium alkoxide compound in percentages by weight of from 0.1 to 10% by weight, preferably 0.5-5% by weight, very particularly preferably 1-2% by weight, based on the total mass of the formulation, in order to achieve particularly good semiconductor layers.

The formulation of the invention further comprises at least one solvent. In order to achieve particularly good formulations, the at least one solvent is preferably selected from the group consisting of primary, secondary, tertiary and aromatic alcohols (the alcohols are particularly preferably methanol, ethanol, butanol, tetrahydrofurfuryl alcohol and phenol), ethers (particular preference is given to glycol ethers of the formula $ROCH_2CH(R')OR''$ where R=—H or —$C_1$-$C_{10}$-alkyl, R'=—H or —$CH_3$ and R''=—H or —$C_1$-$C_{10}$-alkyl and cyclic ethers, in particular 2-methoxyethanol, 1-methoxy-2-propanol and tetrahydrofuran and also anisole), esters (particular preference is given to carboxylic esters and alkyl lactates, in particular butyl acetate, 1-methoxy-2-propyl acetate (PGMEA), ethyl benzoate, ethylene glycol diacetate, ethyl lactate and butyl lactate), aromatic hydrocarbons (particular preference is given to toluene and xylene) and nitriles (particular preference is given to acetonitrile).

The at least one solvent is preferably selected from the group consisting of methanol, ethanol, butanol, tetrahydrofurfuryl alcohol, phenol, 2-methoxyethanol, 1-methoxy-2-propanol, tetrahydrofuran, anisole, butyl acetate, 1-methoxy-2-propyl acetate (PGMEA), ethyl benzoate, ethylene glycol diacetate, ethyl lactate, butyl lactate, toluene, xylene and acetonitrile.

The formulation of the invention more preferably comprises at least two, even more preferably at least three, solvents selected from the group consisting of the above-mentioned classes of solvent.

The formulation of the invention preferably comprises at least three solvents of which one is selected from the group consisting of ethyl lactate, anisole, tetrahydrofurfuryl alcohol, butyl acetate, ethylene glycol diacetate and ethyl benzoate and the other two have a boiling point difference of at least 30° C. under SATP conditions. Particularly good results can be achieved by means of corresponding formulations.

The best results can be achieved using a formulation comprising the three solvents ethanol, 1-methoxy-2-propanol and tetrahydrofurfuryl alcohol.

The formulation of the invention preferably contains the solvent or solvents in percentages by weight of 90-99.9% by weight, preferably 95-99.5% by weight, particularly preferably 98-99% by weight, based on the total mass of the coating composition.

Furthermore, the composition of the invention can comprise additives, in particular wetting additives (in particular surfactants), defoamers, crosslinking additives, surface tension additives and levelling additives in order to achieve advantageous properties. If additives are present, their percentage by weight, based on the total mass of coating composition, is less than 5% by weight, preferably less than 2% by weight. However, the composition of the invention preferably does not comprise any further additives, i.e. it has been produced using exclusively the solvent or solvents and the indium alkoxide compound(s).

To achieve particularly good properties, the formulation is essentially water-free, i.e. it has less than 200 ppm of $H_2O$. Furthermore, the formulation has more preferably been produced using essentially water-free solvents and compounds.

The present invention further provides a process for producing the formulation of the invention, in which at least one of the indium alkoxide compounds mentioned is mixed with at least one solvent.

The indium alkoxide compounds used for producing the formulation of the invention are prepared by means of a process in which an indium trihalide $InX_3$ where X=F, Cl, Br, I
is reacted with a secondary amine of the formula $R'_2NH$ where R'=alkyl,
in a molar ratio of from 8:1 to 20:1 to the indium trihalide
in the presence of an alcohol of the generic formula ROH where R=alkyl.

Indium trihalides of the formula $InX_3$ are known to those skilled in the art and are commercially available.

Secondary amines of the formula R'$_2$NH where R'=alkyl are likewise prior art. The alkyl radical R' is preferably a linear, branched or cyclic C$_1$- to C$_{10}$-alkyl radical of the formula C$_n$H$_{2n+1}$ where n=1 to 10. Two radicals R' of a secondary amine or two different secondary amines can also together form an alkyl radical C$_n$H$_{2n}$. Compounds which can accordingly be used are, for example, dimethylamine, diethylamine, dipropylamine, pyrrolidine, piperidine and pyrrole. Preferred radicals R' are the radicals methyl, ethyl, n-propyl and i-propyl. Very particular preference is given to the radical R' being methyl, since this leads to particularly good yields and particularly stable compounds.

As alcohol ROH preference is given to using alcohols having linear, branched, or cyclic C$_1$ to C$_{10}$-alkyl radicals of the formula C$_n$H$_{2n+1}$ where n=1 to 10. Here too, preferred radicals R are methyl, ethyl, n-propyl and i-propyl. The radicals R are very preferably methyl.

The indium trihalide is preferably used in proportions of from 0.1 to 50% by weight, particularly preferably from 1 to 25% by weight, very particularly preferably from 2 to 10% by weight based on the total mass of all components, in the process.

The indium trihalide can be dissolved, i.e. dissociated or complexed on the molecular level by solvent molecules/alcohol molecules, or dispersed in the liquid phase.

The alcohol ROH is preferably used in proportions of from 50 to 99.9% by weight, particularly preferably 75 to 99% by weight, very particularly preferably from 80 to 96% by weight based on the total mass of all components, in the process.

The reaction mixture of the process can further comprise at least one liquid solvent or dispersion medium which is inert in respect of the reaction, i.e. a solvent/dispersion medium or a mixture of different solvents/dispersion media which does not react with the indium trihalides under the reaction conditions. Preference is given to using aprotic solvents, in particular solvents selected from the group consisting of aprotic nonpolar solvents, i.e. alkanes, substituted alkanes, alkenes, alkines, aromatics without or with aliphatic or aromatic substituents, halogenated hydrocarbons and tetramethylsilane, and the group consisting of aprotic polar solvents, i.e. ethers, aromatic ethers, substituted ethers, esters or acid anhydrides, ketones, tertiary amines, nitromethane, DMF (dimethylformamide), DMSO (dimethyl sulphoxide) and propylene carbonate.

If such a liquid solvent or dispersion medium which is inert in respect of the reaction is present in the reaction mixture, its proportion is preferably from 1 to 50% by weight, particularly preferably from 1 to 25% by weight, very particularly preferably from 1 to 10% by weight based on the total mass of all components.

The secondary amine is preferably used in a molar ratio of from 8:1 to 15:1, even better in a ratio of from 8:1 to 12:1, to the indium trihalide in the reaction, because indium alkoxide compounds which are particularly suitable for layer production can then be prepared in a particularly high yield.

The process of the invention is preferably carried out by initially charging the indium trihalide in an alcohol ROH. The secondary amine is added in gaseous form, liquid form or as a solution in solvents (comprising, in particular, ROH as solvent).

The addition is likewise preferably carried out under SATP conditions (25° C. and 1.013 bar).

Since the reaction can be controlled particularly readily in this way and leads to particularly good indium alkoxide compounds, the dialkylamine is preferably added at a rate of from 0.5 to 5 mol per hour and mol of indium halide, preferably from 1.15 to 2.60 mol per hour and mol of indium halide.

The reaction mixture is more preferably heated after addition of all components in the process. The reaction mixture is preferably heated over a period of from 1 to 10 hours to a temperature in the range from 40 to 70° C. The reaction mixture is more preferably heated over a time of from 1 to 5 hours to a temperature in the range from 45 to 60° C. The reaction mixture is then cooled.

After the reaction is complete, the product or product mixture, which usually precipitates, is preferably separated from the other constituents of the reaction composition. This is preferably effected by filtration. Furthermore, the separated product mixture is preferably dried and washed by means of suitable solvents.

Particularly good indium alkoxide compounds which can be used for producing the formulations of the invention result when the product obtained or the product mixture obtained is recrystallized after separation and possibly drying and/or washing. The recrystallization is preferably carried out in the alcohol ROH which was also used in the synthesis of the compound. The recrystallization is preferably carried out by dissolving the isolated product or product mixture in boiling alcohol and subsequently crystallizing it out at temperatures of from −30 to 0° C. The supernatant solvent is discarded and the crystalline product can be employed for further use.

The formulations of the invention are particularly advantageously suitable for producing indium oxide-containing coatings having improved electrical properties, in particular via wet-chemical processes. This improvement is surprising since substances which have a very low tendency to crystallize are generally sought as precursors of metal oxides. However, the compounds of the invention are often cluster compounds which thus already have a microcrystallite structure. The desired metal oxide layer should tend to have an amorphous rather than crystalline character in order to possess particularly good electrical properties. Contrary to expectations, layers which are particularly homogeneous can be produced using the compound according to the invention.

In this case, the term indium oxide-containing coatings refers both to indium oxide layers and to layers which consist essentially of indium oxide and further metals and/or metal oxides. For the purposes of the present invention an indium oxide layer is a metal-containing layer which can be produced from the indium alkoxides mentioned, and comprises essentially indium atoms or ions, with the indium atoms or ions being present in essentially oxidic form. The indium oxide layer can optionally also comprise proportions of halogen or alkoxide from incomplete conversion and/or nitrogen, hydrogen and/or carbon. An analogous situation also applies to layers which consist essentially of indium oxide and further metals and/or metal oxides, with the proviso that this further comprises the further metals and/or metal oxides.

Furthermore, the formulations of the invention have the surprising advantage that they can be used particularly readily for producing conductive or semiconducting indium oxide-containing layers for electronic components, in particular in the production of (thin film) transistors, diodes or solar cells.

The present invention further provides a process for producing indium oxide-containing layers, in which a formulation according to the invention is applied to an (optionally pre-coated or pre-treated) substrate, optionally dried and converted by means of heat and/or electromagnetic radiation.

The substrate used in these processes according to the invention is preferably a substrate selected from among substrates consisting of glass, silicon, silicon dioxide, a metal oxide or transition metal oxide or a polymeric material, in particular PE, PEN, PI or PET.

After coating and before conversion, the coated substrate can also be dried. Appropriate measures and conditions for this are known to those skilled in the art. However, the coated substrate does not necessarily have to be dried before conversion.

The compositions of the invention are particularly well suited in coating processes selected from among printing processes (in particular flexo/gravure printing, inkjet printing, (reverse) offset printing, digital offset printing and screen printing), spraying processes ("spray coating"), rotational coating processes ("spin coating"), dipping processes ("dipcoating") and other liquid-phase coating processes such as slot die coating processes, slit coating processes, curtain coating processes and doctor-blading processes.

The conversion of the structure or layer produced into indium oxide or an indium oxide-containing layer or structure can be carried out by a thermal route and/or by means of UV, IR or VIS radiation.

However, particularly good results can be achieved when temperatures of from 20° C. to 550° C., preferably from 100 to 400° C., particularly preferably from 150 to 350° C. are used for conversion.

Furthermore, the applied formulation can, as an alternative or in addition, be converted using electromagnetic radiation, in particular UV radiation. Preference is given to conversion using electromagnetic radiation having a wavelength in the range from 160 to 300 nm. Conversion can preferably be effected by means of UVO radiation having significant radiation components in the ranges from 250 to 258 and from 180 to 190 nm, as can be generated, for example, by means of particular mercury vapour lamps. Conversion using radiation from an excimer lamp or an excimer laser, in particular using radiation having a wavelength in the range from 160 to 190 nm, is also possible.

Particularly good layers result when the applied formulation is converted by means of heat (in particular a temperature of from 100 to 400° C., particularly preferably from 150 to 350° C.) and by means of electromagnetic radiation (in particular electromagnetic radiation having a wavelength in the range from 160 to 300 nm).

Conversion times ranging from a few seconds to a number of hours are typically used. Conversion times are typically from 1 s to 24 h, preferably from 10 s to 2 h, more preferably from 1 minute to 40 minutes, particularly preferably from 1 minute to 20 minutes.

Conversion can also be aided by the layer obtained after the coating step being brought into contact with water and/or hydrogen peroxide before the thermal treatment, so that this layer is firstly converted into a metal hydroxide in an intermediate step before the thermal conversion is carried out.

Furthermore, conversion of the applied coating composition can be carried out at normal atmospheric water content.

The quality of the layer produced by the process of the invention can also be improved further by means of a combined thermal and gas treatment (using $H_2$ or $O_2$), plasma treatment (Ar, $N_2$, $O_2$ or $H_2$ plasma), microwave treatment, laser treatment (using wavelengths in the UV, VIS or IR range), UV light, infrared radiation or an ozone treatment after the conversion step.

The following examples illustrate the subject matter of the present invention without having a limiting effect.

EXAMPLE ACCORDING TO THE INVENTION

Synthesis

In a 30 l reactor which has been freed of residual moisture, 1.30 kg of indium(III) chloride ($InCl_3$, 5.9 mol) are suspended under a protective gas atmosphere in 17.38 kg of dried methanol by stirring. Dimethylamine (2.57 kg, 57 mol) is metered in via a mass flow controller (0.86 kg/h, about 4 h) at room temperature, with a slightly exothermic reaction being able to be observed. The reaction mixture is then heated at 50° C. for 2 hours, cooled to room temperature and filtered. The filter residue is washed with 4×500 ml of dried methanol and dried under reduced pressure (0.1 mbar) for 8 hours. The material is dissolved in boiling methanol and crystallized out at −20° C.

Production of a Formulation

The material obtained is dissolved in a concentration of 50 mg/ml in 1-methoxy-2-propanol. The concentrate obtained is formulated as follows: 1 part of concentrate to 2 parts of 1-methoxy-2-propanol to one part of ethanol. 3% by weight of tetrahydrofurfuryl alcohol (THFA) are additionally added to this formulation. All solvents used are water-free (<200 ppm $H_2O$) and mixing is carried out under inert conditions (likewise water-free). The formulation obtained is finally filtered through a 200 nm PTFE filter.

Coating

A doped silicon substrate having an edge length of about 15 mm and an about 200 nm thick silicon oxide coating and finger structures composed of ITO/gold was wetted with 100 µl of the abovementioned formulation. Spin coating at 2000 rpm (30 seconds) is then carried out. The coated substrate is irradiated immediately after this coating operation with UV radiation in the wavelength range of 150-300 nm coming from a mercury vapour lamp for 10 minutes. The substrate is subsequently heated at a temperature of 350° C. on a hotplate for one hour. After conversion, a value for the field effect mobility (in the linear range) pFET=14 $cm^2$/Vs at 2 VDS can be determined in a glove box.

Comparative Example

Synthesis

In a 500 ml round bottom flask which has been freed of residual moisture, 5.0 g of indium(III) chloride ($InCl_3$, 22.5 mmol) are dissolved under a protective gas atmosphere in 250 ml of dried methanol by stirring, leaving a residue of $InCl_3$ of <10% by weight (based on the amount weighed in). The metered addition of the base dimethylamine (5.0 g corresponding to 111 mmol) is ensured by means of a massflow controller and the base is added in the stoichiometric amount based on $InCl_3$ at room temperature over a period of five hours, with a slightly exothermic reaction being observed at the beginning. The solution is subsequently completely evaporated, the solid which remains is taken up into 250 ml of dried methanol, the mixture is filtered under protective gas ($N_2$), the solid is washed a number of times (10 operations) with dried methanol and dried at room temperature under reduced pressure (<10 mbar) for 12 hours. The product yield was >80 mol % of indium(III) chlorodimethoxide.

Production of a Formulation

The material obtained is dissolved in a concentration of 50 mg/ml in 1-methoxy-2-propanol. The concentrate obtained is formulated as follows: 1 part of concentrate to 2 parts of 1-methoxy-2-propanol to one part of ethanol. 3% by weight of tetrahydrofurfuryl alcohol (THFA) are additionally added to this formulation. All solvents used are water-free (<200 ppm $H_2O$) and mixing is carried out under inert conditions (likewise water-free). The formulation obtained is finally filtered through a 200 nm PTFE filter.

Coating

A doped silicon substrate having an edge length of about 15 mm and an about 200 nm thick silicon oxide coating and finger structures composed of ITO/gold was wetted with 100 µl of the abovementioned formulation. Spin coating at 2000 rpm (30 seconds) is then carried out. The coated substrate is irradiated immediately after this coating operation with UV radiation in the wavelength range of 150-300 nm coming from a mercury vapour lamp for 10 minutes. The substrate is subsequently heated at a temperature of 350° C. on a hotplate for one hour. After conversion, a value for the field effect mobility (in the linear range) pFET=8 $cm^2$/Vs at 2 VDS can be determined in a glove box.

The invention claimed is:

1. A liquid formulation, comprising:
   at least one solvent; and
   at least one indium alkoxide compound dissolved in the at least one solvent and having the formula $[In_6(O)(OR)_{12}X_6]^{2-}A_m^z(ROH)_x$,
   where R= alkyl, X= F, Cl, Br, and/or I, A= cation, z= valency of the cation, m·z= 2 and x= 0 to 10.

2. The liquid formulation according to claim 1, wherein the indium alkoxide compound has the formula $[In_6(O)(OMe)_{12}Cl_6]^{2-}[NH_2R_2]^+_2(MeOH)_2$.

3. The liquid formulation according to claim 1, wherein the indium alkoxide compound is included in an amount of from 0.1% to 10% by weight based on the total mass of the liquid formulation.

4. The liquid formulation according to claim 1, wherein the at least one solvent is selected from the group consisting of a primary alcohol, a secondary alcohol, a tertiary alcohol, an aromatic alcohol, an ether, an ester, an aromatic hydrocarbon and a nitrile.

5. The liquid formulation according to claim 1, wherein the at least one solvent is selected from the group consisting of methanol, ethanol, butanol, tetrahydrofurfuryl alcohol, phenol, 2-methoxyethanol, 1-methoxy-2-propanol, tetrahydrofuran, anisole, butyl acetate, 1-methoxy-2-propyl acetate (PGMEA), ethyl benzoate, ethylene glycol diacetate, ethyl lactate, butyl lactate, toluene, xylene and acetonitrile.

6. The liquid formulation according to claim 5, comprising at least three solvents;
   wherein:
   one of the at least three solvents is selected from the group consisting of ethyl lactate, anisole, tetrahydrofurfuryl alcohol, butyl acetate, ethylene glycol diacetate and ethyl benzoate; and
   the other two of the at least three solvents have a boiling point difference of at least 30° C. under standard ambient temperature and pressure conditions.

7. The liquid formulation according to claim 1, comprising three solvents which are ethanol, 1-methoxy-2-propanol and tetrahydrofurfuryl alcohol.

8. The liquid formulation according to claim 1, being essentially water-free.

9. A process for producing the liquid formulation according to claim 1, comprising:
   dissolving the at least one indium alkoxide compound in the at least one solvent.

10. The liquid formulation according to claim 1, wherein the indium alkoxide compound is included in an amount of from 0.1% to 5% by weight based on the total mass of the liquid formulation.

11. The liquid formulation according to claim 1, wherein the indium alkoxide compound is included in an amount of from 0.1% to 2% by weight based on the total mass of the liquid formulation.

12. The liquid formulation according to claim 1, wherein the at least one solvent is included in an amount of from 95% to 99.5% by weight based on the total mass of the liquid formulation.

13. The liquid formulation according to claim 1, wherein the at least one solvent is included in an amount of from 98% to 99.5% by weight based on the total mass of the liquid formulation.

14. The liquid formulation according to claim 1, further comprising:
   at least one additive selected from the group consisting of a wetting additive, a defoamer, a crosslinking additive, a surface tension additive, and a levelling additive,
   wherein the at least one additive is included in an amount of less than 5% by weight.

15. The liquid formulation according to claim 1, consisting of the at least one solvent and the at least one indium alkoxide compound.

* * * * *